(12) United States Patent
Mercenier et al.

(10) Patent No.: US 8,916,145 B2
(45) Date of Patent: Dec. 23, 2014

(54) **USE OF *BIFIDOBACTERIUM LONGUM* FOR THE PREVENTION AND TREATMENT OF INFLAMMATION**

(75) Inventors: Annick Mercenier, Epalinges (CH); Stephanie Blum-Sperisen, Pully (CH); Florence Rochat, Montreux (CH)

(73) Assignee: Nestec S.A., Vevey (CH)

( * ) Notice: Subject to any disclaimer, the term of this patent is extended or adjusted under 35 U.S.C. 154(b) by 1413 days.

(21) Appl. No.: 12/279,472

(22) PCT Filed: Feb. 14, 2007

(86) PCT No.: PCT/EP2007/051448

§ 371 (c)(1),
(2), (4) Date: Oct. 16, 2008

(87) PCT Pub. No.: WO2007/093619

PCT Pub. Date: Aug. 23, 2007

(65) Prior Publication Data

US 2009/0274661 A1    Nov. 5, 2009

(30) Foreign Application Priority Data

Feb. 15, 2006  (EP) .................................. 06101690

(51) Int. Cl.
| | | |
|---|---|---|
| *A01N 63/00* | (2006.01) | |
| *A61K 47/00* | (2006.01) | |
| *A23C 9/12* | (2006.01) | |
| *C12N 1/12* | (2006.01) | |
| *C12N 1/04* | (2006.01) | |
| *A23L 1/30* | (2006.01) | |
| *A23K 1/00* | (2006.01) | |
| *A23K 1/18* | (2006.01) | |
| *A23L 1/29* | (2006.01) | |
| *A61K 35/74* | (2006.01) | |

(52) U.S. Cl.
CPC ............... *A23L 1/3014* (2013.01); *A23K 1/009* (2013.01); *A23K 1/1846* (2013.01); *A23L 1/296* (2013.01); *A61K 35/745* (2013.01)
USPC ....... 424/93.4; 424/439; 435/252.1; 435/260; 426/61; 536/123.1

(58) Field of Classification Search
CPC . A61K 35/745; A61K 35/741; A61K 31/702; A61K 45/06; A61K 38/00; A61K 31/715; A23V 2002/00; A23V 2200/3204; A23V 2250/28; A23L 1/296; A23L 1/3056; A23L 1/3008; A23L 1/09; A23L 1/293; A23L 1/305; A23L 2/66; A23L 1/172; A23L 1/168; A23K 1/009; A23K 1/1643; A23K 1/1853; A23Y 2300/55; A23Y 2300/00; C12Q 1/02
See application file for complete search history.

(56) References Cited

FOREIGN PATENT DOCUMENTS

| | | |
|---|---|---|
| CN | 1678329 | 10/2005 |
| EP | 0199535 | 10/1986 |
| EP | 0577903 | 1/1994 |
| EP | 0768375 | 4/1997 |
| EP | 0862863 | 9/1998 |
| EP | 1384483 | 1/2004 |
| WO | WO 9700078 | 1/1997 |
| WO | WO 0053200 | 9/2000 |
| WO | 2004009103 | 1/2004 |
| WO | WO 2004112507 | 12/2004 |
| WO | WO 2004112509 | 12/2004 |

OTHER PUBLICATIONS

International Search Report for International Application No. PCT/EP2007/051448 mailed on May 25, 2007.
Written Opinion for International Application No. PCT/EP2007/051448 mailed on May 25, 2007.
Abstract of "Physiological Effects of *Bifidobacterium longum* BB536," by N. Ihibashi, Jun. 26, 1996, XP002389907.
Abstract of "*Bifidobacterium longum* BB536 as a probiotic," by Fumiaki Abe, May 15, 2003, XP002389908.
Abstract of "Biologically protective effects and cancer protective effect of *B. longum* BB536," by N. Ihibashi, Sep. 20, 2001, XP002389909.
"Inhibitory Effect of *Bifidobacterium longum* Cultures on the Azoxymethane-Induced Aberrant Crypt Foci Formation and Fecal Bacterial Beta-Glucuronidase (43817)," by N. Kulkarni et al., Proceedings of the Society for Experimental Biology & Medicine, Academic Press Inc., vol. 207, No. 3, 1994, pp. 278-283.
"Stimulation of the Secretion of Pro-Inflammatory Cytokines by *Bifidobacterium* Strains," by He et al., Microbiol. Immunol., 46(11), 2002, pp. 781-785.
"Measurement of cutaneous inflammation: estimation of neutrophil content with an enzyme marker." by P. Bradley et al., Journal of Investigative Dermatology, vol. 78, No. 3, pp. 206-209, 1982.
"Inhibition of leukotriene synthesis markedly accelerates healing in a rat model of inflammatory bowel disease," by J. Wallace et al., Gastroenterology, 1989; 96(1), pp. 29-36.
"Reactivation of hapten-induced colitis and its prevention by anti-inflammatory drugs,"By C. Appleyard et al., Am. J. Physiol., 1995, pp. G119-G125.
"Probiotics: how should they be defined?" by S. Salminem et al., Trends in Food Science & Technology, vol. 10 (1999), pp. 1007-110.

*Primary Examiner* — Iqbal H Chowdhury
(74) *Attorney, Agent, or Firm* — K&L Gates LLP

(57) ABSTRACT

The invention relates to the use, in the manufacture of a medicament or a therapeutic nutritional composition for preventing or reducing inflammation in a mammal, of *bifidobacterium longum* ATCC BAA-999.

12 Claims, 7 Drawing Sheets

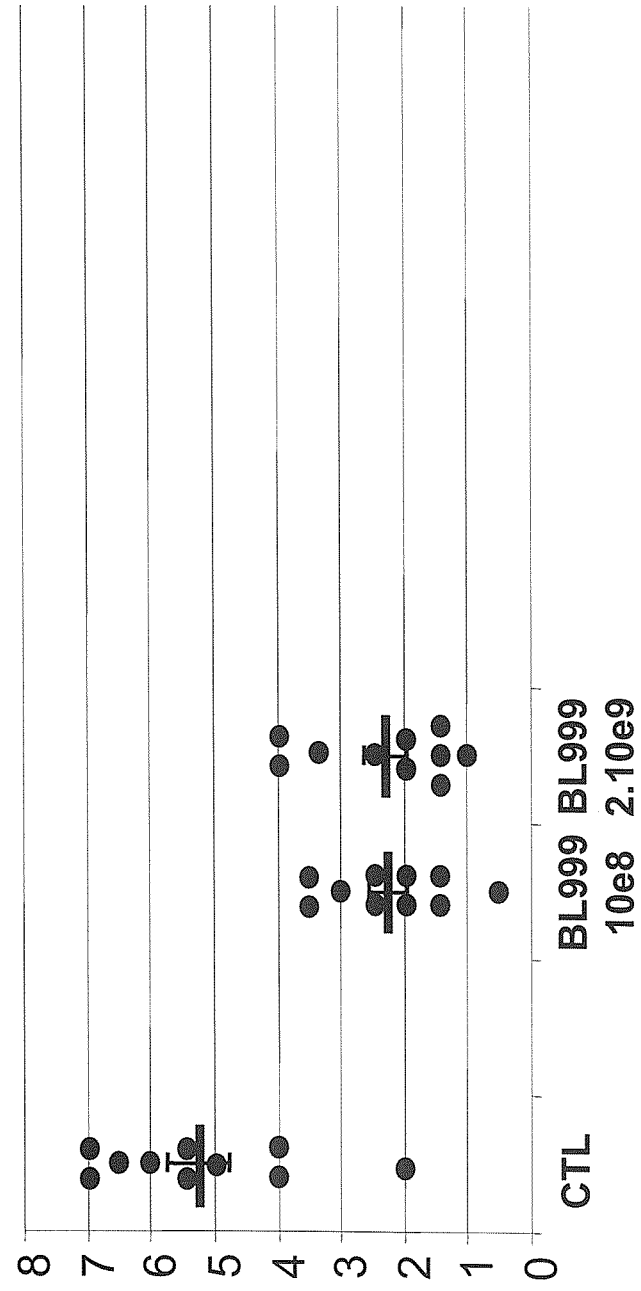

Figure 1:
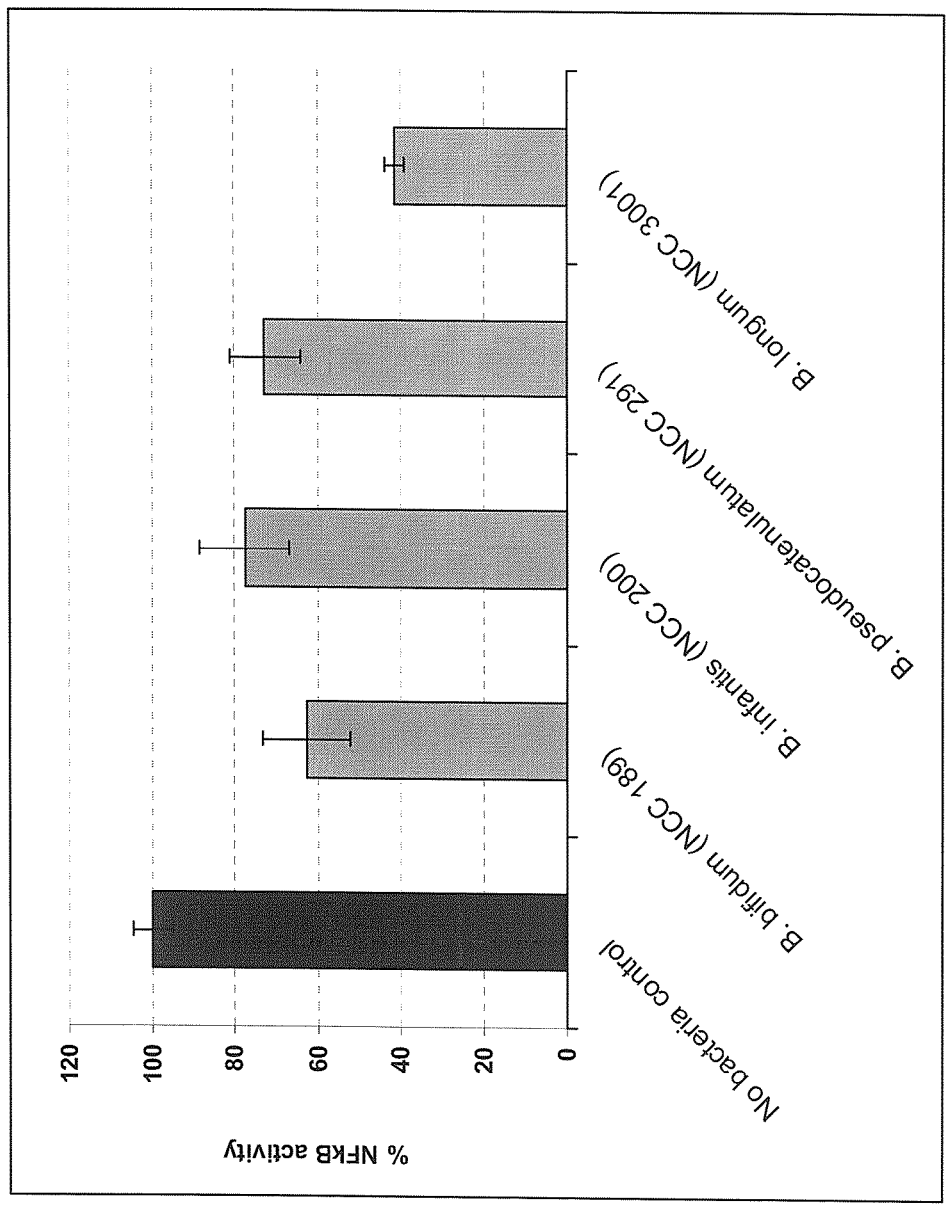

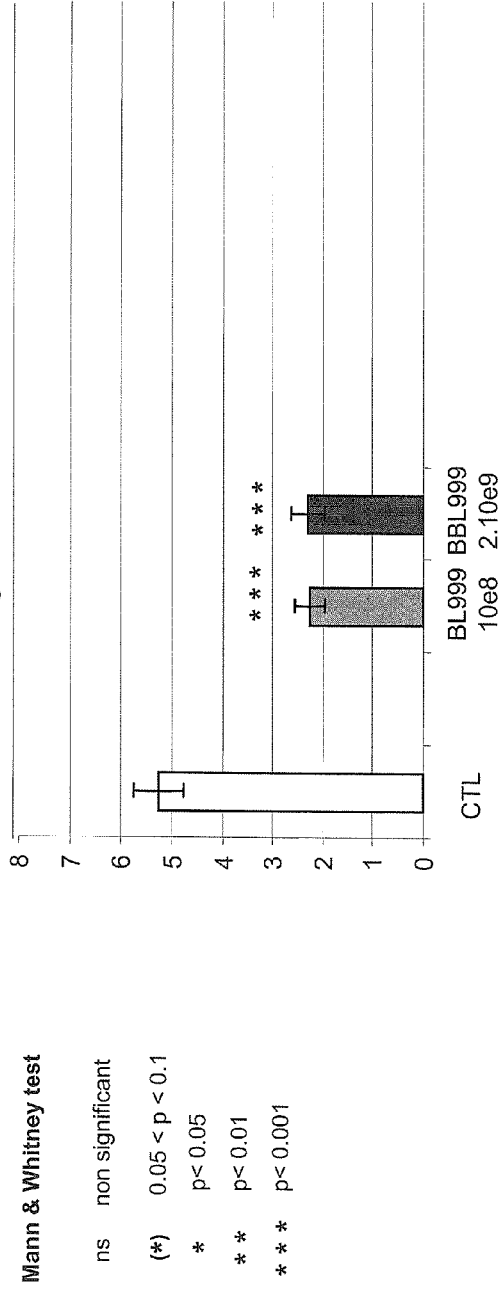
Fig 4B. Mean Wallace score
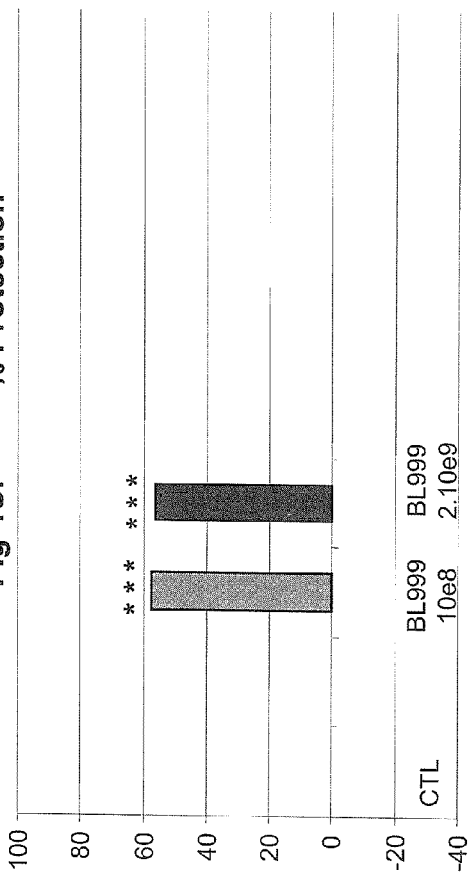
Fig 4C. % Protection
Mann & Whitney test
ns  non significant
(*)  0.05 < p < 0.1
*    p < 0.05
**   p < 0.01
***  p < 0.001

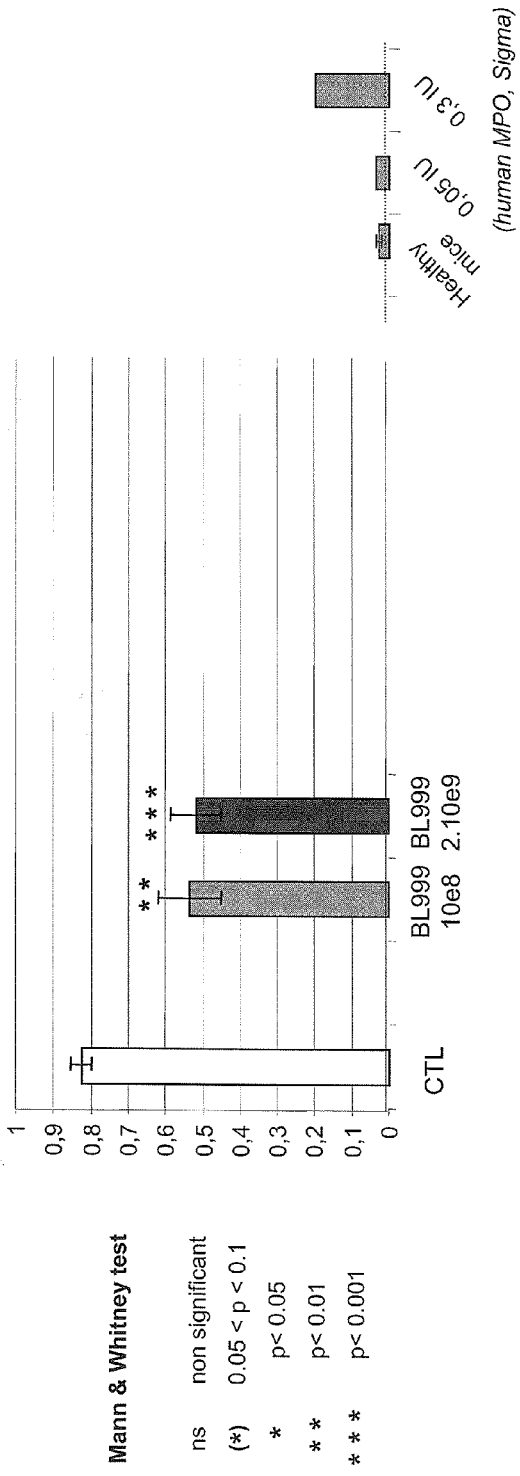
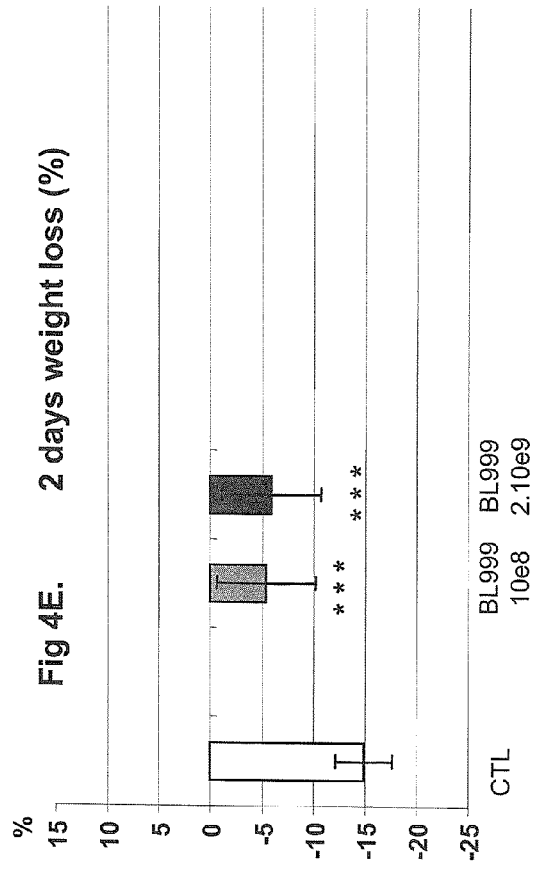

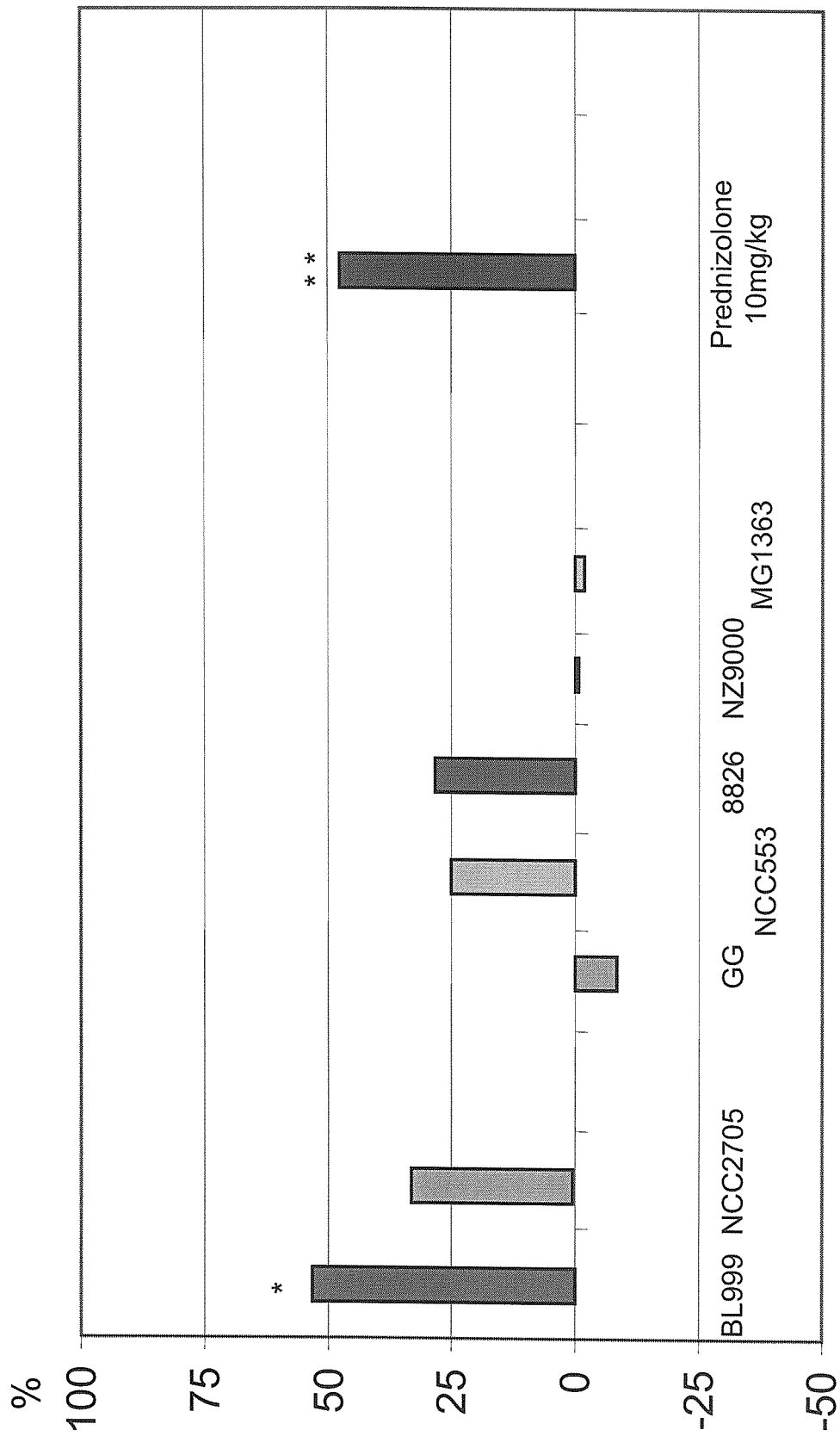
Fig 5. % of Protection against TNBS-induced colitis (expressed as the mean of 2-3 experiments)

USE OF *BIFIDOBACTERIUM LONGUM* FOR THE PREVENTION AND TREATMENT OF INFLAMMATION

This invention relates to a method for the prevention and treatment of inflammation.

In the recent past, certain strains of bacteria have attracted considerable attention because they have been found to exhibit valuable properties for man if ingested. In particular, specific strains of the genera *Lactobacillus* and *Bifidobacterium* have been found to be able to establish themselves in the intestinal tract and transiently colonise the intestine, to reduce the adherence of pathogenic bacteria to the intestinal epithelium, to have immunomodulatory effects and to assist in the maintenance of well-being. Such bacteria are commonly called probiotics.

Extensive studies have been carried out to identify new probiotic strains. For example, EP 0 199 535, EP 0 768 375, WO 97/00078, EP 0 577 903 and WO 00/53200 disclose specific strains of lactobacilli and bifidobacteria and their beneficial effects.

Inflammation is a complex reaction of the innate immune system that involves the accumulation and activation of leucocytes and plasma protein at sites of infection, toxin exposure or cell injury. Although inflammation serves as a protective function in controlling infections and promoting tissue repair, it can also cause tissue damage and disease. Gastrointestinal diseases such as inflammatory bowel disease (for example Crohn's disease, ulcerative colitis, and pouchitis), food allergies and atopic dermatitis resulting from food allergies are always accompanied by aberrant intestinal inflammatory responses at different levels. The alleviation of this intestinal inflammation by balancing pro- and anti-inflammatory cytokines or induction of regulatory cytokines has been suggested as a possible treatment for these chronic diseases. There are numerous such cytokines of which IFN-γ, IL1, IL8, IL12 and TNF-α for example are regarded as pro-inflammatory and IL10 and TGF-β for example are regarded as anti-inflammatory.

Macrophages are tissue based phagocytic cells derived from monocytes which play an important role in the innate immune response. They are activated by microbial components and, once activated can themselves secrete both pro- and anti-inflammatory cytokines. In "Stimulation of the Secretion of Pro-Inflammatory Cytokines by *Bifidobacterium* Strains" (Microbiol. Immunol., 46(11), 781-785, 2002) He et al investigated the ability of different bifidobacteria strains to affect the production of macrophage derived cytokines. They discovered that "adult type" bifidobacteria such as *Bifidobacterium adolescentis* and *Bifidobacterium longum* induced significantly more pro-inflammatory cytokine secretion than did "infant type" bifidobacteria such as *Bifidobacterium bifidum, Bifidobacterium breve* and *Bifidobacterium infantis*. In addition they noted that *B. adolescentis* in particular did not stimulate production of the anti-inflammatory cytokine IL-10. They concluded that adult-type bifidobacteria may be more potent to amplify, but less able to down-regulate, the inflammatory response.

More recently, attempts to identify the most promising anti-inflammatory probiotic strains for human use have indicated that the generalizations made by He et al are likely to prove unreliable as it has now been demonstrated that the properties of a specific strain—for example its anti-inflammatory properties—cannot be accurately predicted by reference to its taxonomic classification.

SUMMARY OF THE INVENTION

The present inventors have surprisingly discovered that a specific probiotic strain of *B. longum*, namely *Bifidobacterium longum* ATCC BAA-999, has exceptional anti-inflammatory properties.

Accordingly, the present invention provides the use of *Bifidobacterium longum* ATCC BAA-999 in the manufacture of a medicament or therapeutic nutritional composition for preventing or reducing inflammation in a mammal.

The invention further extends to a method of preventing or reducing inflammation in a mammalian patient in need thereof which comprises administering to the patient a therapeutic amount of *Bifidobacterium longum* ATCC BAA-999.

The present invention may be used in circumstances where it is desired to prevent or reduce intestinal inflammation irrespective of the underlying condition which may be, for example, a reaction to a food allergen, chronic or acute intestinal inflammation caused by a disease of the gastrointestinal tract such as inflammatory bowel disease or colitis, post-infective inflammation or chronic sub-clinical inflammation in the elderly as well as in circumstances where it is desired to prevent inflammation in the sense of prophylaxis i.e. where there is no underlying condition giving rise to inflammation.

An advantage of the present invention is that it may be used to reduce or prevent inflammation in a mammal by oral administration of a therapeutic nutritional composition or medicament incorporating the probiotic. It will be appreciated that such oral administration is more acceptable and convenient for the patient than a composition requiring intravenous or subcutaneous administration which not only requires specially trained personnel, but also is neither as safe nor as convenient.

DETAILED DESCRIPTION OF THE INVENTION

In the present specification, the following words are given a definition that must be taken into account when reading and interpreting the description, examples and claims.

"Infant": child under the age of 12 months;

"Infant formula": foodstuff intended for the complete nutrition of infants during the first four to six months of life and as a complement to other foodstuffs up to the age of 12 months.

"Probiotic": microbial cell preparations or components of microbial cells with a beneficial effect on the health or well-being of the host. (Salminen S, Ouwehand A. Benno Y. et al "Probiotics: how should they be defined" Trend Food Sci. Technol. 1999:10 107-10).

The mammal may be a human or a companion animal such as a dog or cat.

The *Bifidobacterium longum* ATCC BAA-999 ("BL999") may be administered on its own, for example enclosed in capsules each containing, for example, 108 colony forming units (cfu) or incorporated in a nutritional composition such as a nutritionally complete formula (for example an infant formula or a clinical nutrition product), a dairy product, a beverage powder, a dehydrated soup, a dietary supplement, a meal replacement, a nutritional bar, a cereal, a confectionery product or a dry pet food. When incorporated in a nutritional composition, BL999 may be present in the composition in an amount equivalent to between $10^4$ and $10^{12}$ cfu/g (dry weight). These expressions of quantity include the possibilities that the bacteria are live, inactivated or dead or even present as fragments such as DNA or cell wall materials or as metabolites. In other words, the quantities of bacteria are expressed in terms of the colony forming ability of that quantity of bacteria as if all the bacteria were live irrespective of whether they are, in fact, live, inactivated or dead, fragmented or a mixture of any or all of these states. Preferably the BL999 is present in an amount equivalent to between $10^5$ to $10^{10}$ more preferably $10^7$ to $10^{10}$ cfu/g of dry composition.

BL999 may be obtained from Morinaga Milk Industry Co. Ltd. of Japan under the trade mark BB536. It may be cultured according to any suitable method and prepared for encapsulation or addition to a nutritional composition by freeze-drying or spray-drying for example. Alternatively, it may be purchased already prepared in a suitable form for addition to food products.

A nutritionally complete formula for use in the present invention may comprise a source of protein, preferably a dietary protein such as an animal protein (for example milk, meat or egg protein), a vegetable protein (for example soy, wheat, rice or pea protein); mixtures of free amino acids; or combinations thereof. Milk proteins such as casein and whey protein and soy proteins are particularly preferred. The composition may also contain a source of carbohydrates and a source of fat.

If the formula includes a fat source, it preferably provides 5% to 55% of the energy of the formula; for example 20% to 50% of the energy. The lipids making up the fat source may be any suitable fat or fat mixture. Vegetable fats such as soy oil, palm oil, coconut oil, safflower oil, sunflower oil, corn oil, canola oil, and lecithins are particularly suitable. Animal fats such as milk fat may also be added if desired.

If the formula includes a carbohydrate source, it preferably provides 40% to 80% of the energy of the formula. Any suitable carbohydrate may be used, for example sucrose, lactose, glucose, fructose, corn syrup solids, maltodextrins, and mixtures thereof. Dietary fibre may also be added if desired. The dietary fibre may be from any suitable origin, including for example soy, pea, oat, pectin, guar gum, gum Arabic, fructooligosaccharides, galacto-oligosaccharides, sialyl-lactose and oligosaccharides derived from animal milks. Suitable vitamins and minerals may be included in the nutritional formula in an amount to meet the appropriate guidelines.

One or more food grade emulsifiers may be incorporated into the nutritional formula if desired; for example diacetyl tartaric acid esters of mono- and di-glycerides, lecithin and mono- and di-glycerides. Similarly suitable salts and stabilisers may be included.

The nutritionally complete formula may be prepared in any suitable manner. For example, the protein source, the carbohydrate source, and the fat source may be blended together in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to a temperature in the range from about 60° C. to about 85° C.; for example by flash cooling. The liquid mixture may then be homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture is conveniently standardised at this point.

The homogenised mixture may then be transferred to a suitable drying apparatus such as a spray drier or freeze drier and converted to powder. The powder should have a moisture content of less than about 5% by weight. The BL999 may be added to the powder in the desired quantity by dry mixing.

A dry pet food for use in the present invention may include any one or more of a carbohydrate source, a protein source and lipid source.

Any suitable carbohydrate source may be used. Preferably the carbohydrate source is provided in the form of grains, flours or starches. For example, the carbohydrate source may be rice, barley, sorghum, millet, oat, corn meal or wheat flour. Simple sugars such as sucrose, glucose and corn syrups may also be used. The amount of carbohydrate provided by the carbohydrate source may be selected as desired. For example, the pet food may contain up to about 60% by weight of carbohydrate.

Suitable protein sources may be selected from any suitable animal or vegetable protein source; for example muscular or skeletal meat, meat and bone meal, poultry meal, fish meal, milk proteins, corn gluten, wheat gluten, soy flour, soy protein concentrates, soy protein isolates, egg proteins, whey, casein, gluten, and the like. For elderly animals, it is preferred for the protein source to contain a high quality animal protein. The amount of protein provided by the protein source may be selected as desired. For example, the pet food may contain about 12% to about 70% by weight of protein on a dry basis.

The pet food may contain a fat source. Any suitable fat source may be used. Preferably the fat source is an animal fat source such as tallow. Vegetable oils such as corn oil, sunflower oil, safflower oil, rape seed oil, soy bean oil, olive oil and other oils rich in monounsaturated and polyunsaturated fatty acids, may also be used. In addition to essential fatty acids (linoleic and alpha-linoleic acid) the fat source may include long chain fatty acids. Suitable long chain fatty acids include, gamma linoleic acid, stearidonic acid, arachidonic acid, eicosapentanoic acid, and docosahexanoic acid. Fish oils are a suitable source of eicosapentanoic acids and docosahexanoic acid. Borage oil, blackcurrant seed oil and evening primrose oil are suitable sources of gamma linoleic acid. Rapeseed oil, soybean oil, linseed oil and walnut oil are suitable sources of alpha-linolenic acid. Safflower oils, sunflower oils, corn oils and soybean oils are suitable sources of linoleic acid. Olive oil, rapeseed oil (canola), high oleic sunflower oil, safflower oil, peanut oil, and rice bran oil are suitable sources of monounsaturated fatty acids. The amount of fat provided by the fat source may be selected as desired. For example, the pet food may contain about 5% to about 40% by weight of fat on a dry basis. Preferably, the pet food has a relatively reduced amount of fat.

The choice of the carbohydrate, protein and lipid sources is not critical and will be selected based upon nutritional needs of the animal, palatability considerations, and the type of product produced. Further, various other ingredients, for example, sugar, salt, spices, seasonings, vitamins, minerals, flavoring agents, gums, and probiotic micro-organisms may also be incorporated into the pet food as desired.

For elderly pets, the pet food preferably contains proportionally less fat than pet foods for younger pets. Further, the starch sources may include one or more of oat, rice, barley, wheat and corn.

The pet food may be produced by extrusion cooking, although baking and other suitable processes may be used. When extrusion cooked, the pet food is usually provided in the form of a kibble. The BL999 is preferably coated onto or filled into the dried pet food. A suitable process is described in European Patent Application No 0862863.

The invention will now be further described by the reference to the following examples. In the Figures:—

Figure 2:
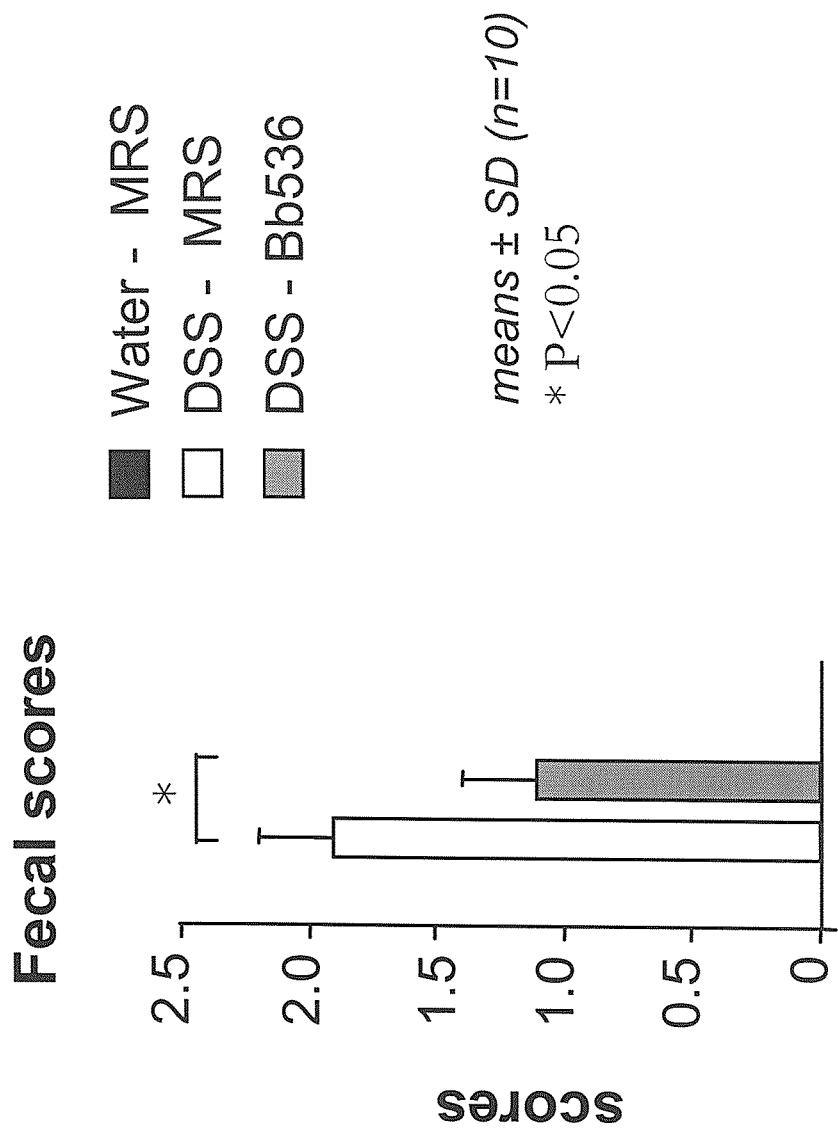
Figure 3:
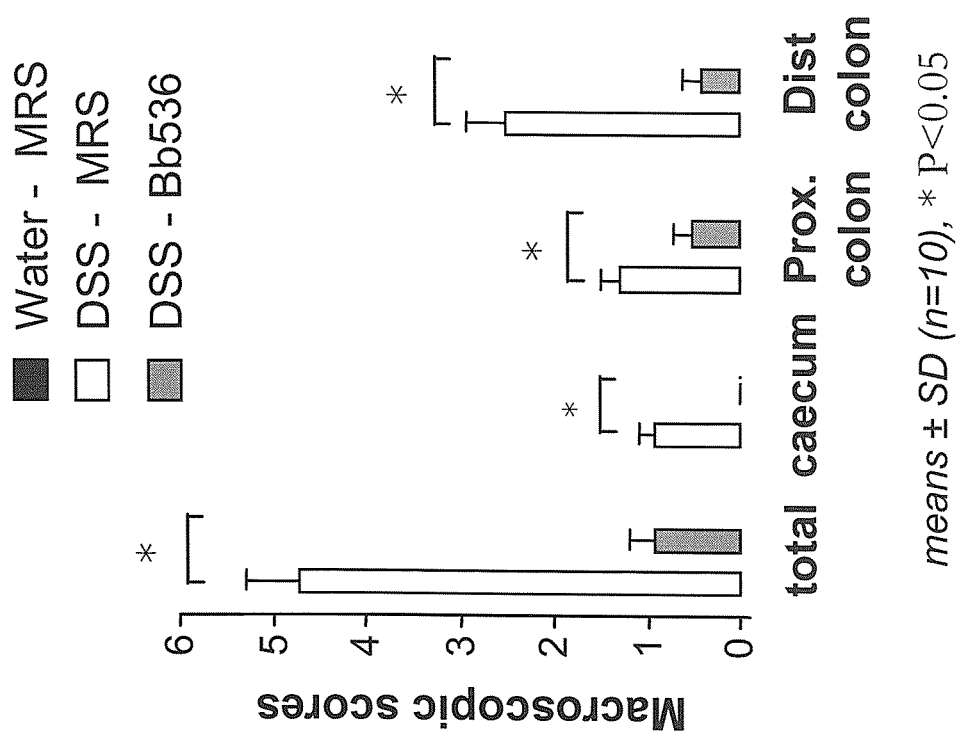

FIG. 1 compares the percentage of NFκB activity after stimulation of intestinal cells in vitro with LPS in the presence of four different bifidobacteria (cell based NFκB reporter gene assay);

FIG. 2 compares the fecal score observed in a mouse colitis model mimicking IBD pathologies (DSS induced colitis) with and without intervention with BL999;

FIG. 3 compares the macroscopic inflammation scores observed in a mouse colitis model mimicking IBD pathologies (DSS induced colitis) with and without intervention with BL999;

FIG. 4A to E compare the individual Wallace scores (A), the mean Wallace scores (B), the percentage protection (C), the myeloperoxidase activity (D) and the two day weight loss (E) observed in a TNBS-induced model of colitis wherein two groups received an intervention with BL999 at different dosage levels and the control group received no bacteria; and FIG. 5 compares the protective capacity of BL999 in the same mouse colitis model to those of *B. longum* NCC2705, *L. rhamnosus* ATCC 53103, *L. johnsonii* CNCM I-1225, *L. plantarum* NCIMB8826, *L. lactis* NZ9000 and MG1363; and to the protective effect of the medicament prednisolone.

EXAMPLE 1

An example of the composition of an infant formula for use in the present invention is given below. This composition is given by way of illustration only.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| *B. longum* BB 536 | $10^8$ cfu/g of powder, live bacteria | |

EXAMPLE 2

This example compares the inhibitory activity of BL999 with the inhibitory effects of other probiotic bacterial strains in a nuclear factor kappa B (NFκB) cell-based reporter gene assay.

An abundance of literature has been published on the central role that the transcription factor NFκB plays in the induction and perpetuation of inflammatory events. NFκB is activated in response to entero-invasive pathogenic bacteria and other inflammatory stimuli which lead to the production of inflammatory molecules, such as tumor necrosis factor-α (TNF-α), interleukin-8 (IL-8), intracellular adhesion molecule-1 (ICAM-1), and inducible cyclo-oxygenase (COX-2).

A human intestinal epithelial cell line (HT29 NFκB) stably expressing a reporter gene construct (secreted alkaline phosphatase) under the control of the endogenous NFκB promoter was used in this study (Blum S et al.; Riedel C. et al. World J Gastroenterol. 2006 in press). The ability of four bifidobacteria strains to inhibit lipopolysaccharide (LPS)-induced NFκB activity in these cells was measured. Cells were incubated with freshly prepared *B. bifidum* (NCC 189, CNCM 1-2333), *B. infantis* (NCC 200, CNCM 1-2334), *B. pseudocatenulatum* (NCC 291), and *B. longum* (NCC 3001, ATCC BAA-999) at a cell to bacteria ratio of 1:100. Following 1 hr pre-incubation of cells with bacteria, LPS at 10 ng/ml was added for an additional 4 hrs and spent culture supernatants were collected for measurement of NFκB-mediated reporter activity. The assay was done in duplicate and repeated at least 3 times with each repetition normalized to LPS stimulation without bacteria, no bacteria control. The data are shown in FIG. 1 as the mean percentage of LPS-stimulated NFκB activity±SEM.

It may be seen that cells treated with LPS had a 10-fold induction in NFκB activity following 4 hrs of incubation. All four bifidobacteria strains down-modulated NFκB activity, however, BL999 had the greatest inhibitory activity in this assay. In conclusion, BL999 is an excellent candidate strain for applications where inhibition of inflammatory activity is of great value.

EXAMPLE 3

This example demonstrates the capability of BL999 and its metabolites to prevent inflammation in a mouse model of IBD.

A dextran sodium sulphate (DSS)-induced mouse model of colitis recognized as a relevant model for IBD pathologies was used in this experiment (Blumberg R S et al, Current Opin. Immunol. 1999; 11(6):648-56). Administration of DSS induces histopathological damage in the large intestine similar to that observed in ulcerative colitis patients. The DSS treatment was administered so as to induce acute intestinal inflammation.

Experimental Groups and Diets:
"Control-MRS": mice fed the control diet (Table 1) ad libitum, with free access to tap water during the whole experiment, and receiving a daily intra-gastric gavage of MRS from day 1 to day 14

"DSS-MRS": mice fed the control diet ad libitum during the whole experiment, with free access to tap water containing 1% DSS from day 7 to day 14, and receiving a daily intra-gastric gavage of MRS from day 1 to day 14

"DSS-BL": mice fed the control diet during the whole experiment, from day 1 to day 14, with free access to tap water containing 1% DSS from day 7 to day 14, and receiving a daily intragastric gavage of BL999 (NCC3001) ($10^9$ cfu/mouse/day) from day 1 to day 14

TABLE 1

| Control diet | |
|---|---|
| Components | Percentage in the diet (wt %) |
| Resistant starch (Cerestar SF 12018) | 40.0 |
| Soluble casein | 20.0 |
| Saccharose | 27.3 |
| DL-methionine | 0.3 |
| Corn oil | 5.0 |
| Cellulose | 2.0 |
| Mineral premix AIN 93 | 4.4 |
| Vitamin premix AIN 93 | 1.0 |

The animal experiment was conducted as follows. Male BALBc/J mice (8 weeks, Janvier, France) were randomised into 4 experimental groups (n=10 mice per group). During a 7 days acclimatisation period, mice had free access to tap water and received the control diet. Then, mice in Group DSS-BL received a daily intra-gastric gavage of BL999 ($10^9$ cfu/mouse/day) with the culture supernatant for 14 days whilst mice in the other two groups received a daily intra-gastric gavage of MRS. In addition, from day 7 to day 14, mice in both the DSS-MRS and DSS-BL groups received 1% DSS in their drinking water while the Control group received normal tap water.

Every 2 days during the experiment, fecal samples from each mouse were examined and the consistency, and presence or absence of blood was recorded (Hemoccult II, SKD, Roissy, France). A fecal score was calculated as indicated in Table 2 and the results are shown in FIG. 2.

TABLE 2

| Scale followed to score mice clinical symptoms. | |
|---|---|
| Intensity scores Stool scores | Observations |
| 0 | Normal, hard |
| 1 | Soft, well formed, sticky |
| 2 | Not formed |
| 3 | Liquid, diarrhea |

At the end of the 14 day period, mice were sacrificed by cervical dislocation. The caeco-colic segments were rapidly removed from the animal, gently washed with a physiological saline buffer, and scored for macroscopic inflammatory signs following adaptation of the scale previously published by Appleyard and Wallace (Appleyard C. B and Wallace J. L. "Reactivation of hapten-induced colitis and its prevention by anti-inflammatory drugs" Am J. Physiol 269, G119-125) (Table 3). The results are shown in FIG. 3.

TABLE 3

| Criteria for macroscopic scoring of caeco-colonic damage (Appleyard and Wallace) | | |
|---|---|---|
| | Score | Appearance |
| Thickening | 0 | Normal mucosa |
| | 1 | Moderate thickening |
| | 2 | Severe thickening |
| Ulcerations | 0 | None |
| | 1 | Rednesses |
| | 2 | Slight ulcerations |
| | 3 | Strong ulcerations |

TABLE 3-continued

| Criteria for macroscopic scoring of caeco-colonic damage (Appleyard and Wallace) | | |
|---|---|---|
| | Score | Appearance |
| Caeco-colic contents | 0 | No blood |
| | 1 | Slightly bloody |
| | 2 | Bloody |

From FIGS. 2 and 3, it may be seen that the BL999 effectively normalizes the stool characteristics and significantly reduces inflammation in the caecum and proximal and distal colon compared with that observed in the DSS-MRS group. Thus it may be seen that BL999 is effective in preventing the DSS-induced inflammation as the mice in group DSS-BL received bacteria both before and during administration of the DSS.

EXAMPLE 4

In this example, the anti-inflammatory potential of BL999 bacteria was investigated and compared with that of other strains of lactic acid bacteria as well as prednisolone, a commonly used anti-inflammatory drug, using a mouse model of acute colitis induced by TNBS.

The following strains bacterial strains were investigated:—

| NCC No | Strain | Official Deposit No. |
|---|---|---|
| NCC 3001 | Bifidobacterium longum | ATCC BAA-999 |
| NCC 2705 | Bifidobacterium longum | CNCM I-2618 |
| NCC 3003 | Lactobacillus rhamnosus | ATCC 53103 |
| NCC 533 | Lactobacillus johnsonii | CNCM I-1225 |
| | Lactobacillus plantarum | NCIMB8826 |
| | Lactococcus lactis | NZ9000 |
| | Lactococcus lactis | MG1363 |

*Lactobacillus* strains were grown aerobically at 37° C. in MRS medium (Difco). Bifidobacteria were grown anaerobically at 37° C. in MRS supplemented with 0.05% L-cysteine hydrochloride (Sigma). *Lactococcus lactis* MG1363 and *Lactococcus lactis* NZ9000 were grown at 30° C. in M17 medium supplemented with 0.5% glucose. The number of bacteria (cfu) was estimated at stationary growth phase by measuring the absorbance at 600 nm ($A_{600}$), with respective calibration curve for each strain. For routine in vivo experiments, bacteria were grown for 18 h, washed twice in sterile PBS pH 7.2 and re-suspended at 108 and $2.10^9$ cfu/ml in 0.2 M $NaHCO_3$ buffer containing 2% glucose.

Adult female BALB/C mice aged 7 to 8 weeks were purchased from Charles River. The mice were randomised into experimental groups with 10 mice per group. Mice were group housed (8 to 10 per cage) and had free access to water and standard rodent chow. They underwent at least 1 week of acclimatization before any intervention. Mice in the groups treated with bacteria received bacterial suspensions (corresponding to $10^8$ cfu/mouse/day) by intra-gastric gavage in 0.2M $NaHCO_3$ buffer at pH 8.5 with 2% glucose from the fourth day before induction of colitis to the day of induction of colitis. Mice in the group treated with prednisolone received 10 mg/kg body weight/day. Mice in the control group received no bacteria or prednisolone. Further, the effect of dosage level was investigated by treating one group with BL999 at $2.10^9$ cfu/mouse/day.

Prior to induction of colitis, all mice were anaesthetized by intraperitoneal injection of 3 mg of ketamine (Imalgene 1000, Merial, Lyon, France), 46.7 μg of diazepam (Valium, Roche Diagnostics, France) and 15 μg of atropine (Aguettant Laboratory, Lyon, France) dissolved in 0.9% sodium chloride. Then colitis was induced by intra-rectal administration of 50 μl of trinitrobenzene sulphonic acid (TNBS, Fluka, France) dissolved in 0.9% NaCl/ethanol (50/50 v/v) at a dose of 100-120 mg/kg of body weight. Mortality rate and inflammation scores were assessed 48 hours after TNBS administration. Mice were weighed prior to administration of TNBS and at sacrifice which was performed by cervical dislocation.

The colon was removed, dissected free of fat and mesenterium, carefully opened and cleaned with PBS. Colonic damage and inflammation were assessed according to the Wallace criteria (Wallace J. L. et al, Inhibition of leukotriene synthesis markedly accelerates healing in a rat model of inflammatory bowel disease" Gastroenterology 96:29-36, 1989). These criteria for macroscopic scoring have been well established in mouse studies and reflect the intensity of inflammation, the thickening of colonic mucosa and the extent of ulceration. Colonic damage and inflammation were scored blind by two researchers.

In addition, myeloperoxidase (MPO) activity, a marker of polymorphonuclear neutrophil primary granules, was determined according to a modified method of Bradley et al. ("Measurement of cutaneous inflammation: estimation of neutrophil content with an enzyme marker" J Invest Dermatol. 60(3):618-22). Protein concentration was determined by the method of Lowry, and MPO activity expressed as U MPO/cm of intestine.

MPO activity was determined in proximal colon tissue, immediately after sacrifice. A colonic sample (1 cm long) was taken at 3 cm from the caeco-colonic junction, suspended in potassium phosphate buffer (50 mmol/L, pH 6.0) and homogenized in ice using a polytron. Three cycles of freezing and thawing were performed and suspensions were centrifuged at 10,000 g for 15 min at 4° C. Supernatants were discarded and pellets were re-suspended in the detergent hexadecyl trimethylammonium bromide buffer (HTAB 0.5%, w/v, in 50 mmol/L potassium phosphate buffer, pH 6.0), inducing the release of MPO from the polymorphonuclear neutrophil primary granules. Suspensions obtained were sonicated on ice, and again centrifuged for 15 min at 4° C. Supernatants were diluted in potassium phosphate buffer (pH 6.0) containing 0.167 mg/mL of O-dianisidine dihydrochloride and 0.0005% of hydrogen peroxide ($H_2O_2$). MPO from human neutrophils (0.1 U/100 mL, Sigma) was used as a standard. Changes in absorbance at 450 nm, over 5 and 10 min, were recorded with a microplate spectrophotometer (ELX808, Bio-Tek Instrument, CA). One unit of MPO activity was defined as the quantity of MPO degrading 1 mmol hydrogen peroxide/min/mL at 25° C.

Results were analyzed by the non-parametric one-way analysis of variance, Mann-Whitney U test. Differences were judged to be statistically significant when the p value was <0.05.

The results are shown in FIG. 4, A to E and FIG. 5. FIGS. 4 A and B compare the individual Wallace scores and the mean Wallace scores of mice treated with BL999 at the two dosage levels, $10^8$ cfu/mouse/day and $2.10^9$ cfu/mouse/day with the control group who received no bacteria. It may be seen that mice from both the groups which received BL999 had substantially lower Wallace scores than mice in the control group.

FIG. 4C shows the percentage protection provided by the BL999. This corresponds to the reduction of the mean macroscopic inflammation of bacteria-treated mice (n=10) in relation to the mean score of TNBS-treated control mice ($NaOHCO_3$ buffer-treated mice, n=10).

FIG. 4D compares the mean MPO activity of mice treated with BL999 at the two dosage levels with the control group. It may be seen that mice from both the groups which received BL999 had substantially lower MPO activity than mice in the control group.

FIG. 4E compares the 2 day weight loss of mice treated with BL999 at the two dosage levels with the control group. It may be seen that mice from both the groups which received BL999 had substantially lower weight loss than mice in the control group.

FIG. 5 compares the percentage protection provided by the various strains of lactic acid bacteria tested and by administration of prednisolone. It may be seen that BL999 provides a markedly greater degree of protection than the other bacterial strains tested and a comparable level of protection to the medicament.

The invention claimed is:

1. A method of manufacture of a medicament or therapeutic nutritional composition for treating or reducing inflammation in a mammal, the method comprising adding *Bifidobacterium longum* ATCC BAA-999 to a medicament or therapeutic nutritional composition to produce the medicament or therapeutic nutritional composition, the medicament or therapeutic nutritional composition having a fat source that provides 5% to 55% of the energy and a carbohydrate source that provides 40% to 80% of the energy of the medicament or therapeutic nutritional composition, wherein the medicament or therapeutic nutritional composition contains from $10^8$ to $10^{12}$ cfu/g of *Bifidobacterium longum* ATCC BAA-999 on a dry weight basis.

2. The method of claim 1, wherein the medicament or therapeutic nutritional composition is an infant formula.

3. The method of claim 1, wherein the medicament or therapeutic nutritional composition is a pet food.

4. The method of claim 1, wherein the inflammation is intestinal inflammation.

5. A method of manufacture of a medicament or therapeutic nutritional composition for treating inflammatory bowel disease, the method comprising adding *Bifidobacterium longum* ATCC BAA-999 to a medicament or therapeutic nutritional composition to produce the medicament or therapeutic nutritional composition, the medicament or therapeutic nutritional composition having a fat source that provides 5% to 55% of the energy and a carbohydrate source that provides 40% to 80% of the energy of the medicament or therapeutic nutritional composition, wherein the medicament or therapeutic nutritional composition contains from $10^8$ to $10^{12}$ cfu/g of *Bifidobacterium longum* ATCC BAA-999 on a dry weight basis.

6. A method of manufacture of a medicament or therapeutic nutritional composition for reducing intestinal inflammation associated with food allergies, the method comprising adding *Bifidobacterium longum* ATCC BAA-999 to a medicament or therapeutic nutritional composition to produce the medicament or therapeutic nutritional composition, the medicament or therapeutic nutritional composition having a fat source that provides 5% to 55% of the energy and a carbohydrate source that provides 40% to 80% of the energy of the medicament or therapeutic nutritional composition, wherein the medicament or therapeutic nutritional composition contains from $10^8$ to $10^{12}$ cfu/g of *Bifidobacterium longum* ATCC BAA-999 on a dry weight basis.

7. The method of claim 3, wherein the pet food contains about 12% to about 70% by weight of protein on a dry basis.

8. The method of claim 3, wherein the pet food contains about 5% to about 50% by weight of fat on a dry basis.

9. The method of claim 1, wherein the medicament or therapeutic nutritional composition is selected from the group consisting of: a dehydrated soup, a dietary supplement, a meal replacement, a nutritional bar, a cereal and a confectionery product.

10. The method of claim 1, wherein the *Bifidobacterium longum* ATCC BAA-999 is the only probiotic in the medicament or therapeutic nutritional composition.

11. The method of claim 5, wherein the *Bifidobacterium longum* ATCC BAA-999 is the only probiotic in the medicament or therapeutic nutritional composition.

12. The method of claim 5, wherein the *Bifidobacterium longum* ATCC BAA-999 is the only probiotic in the medicament or therapeutic nutritional composition.

\* \* \* \* \*